US011219895B2

(12) United States Patent
Zamzami et al.

(10) Patent No.: US 11,219,895 B2
(45) Date of Patent: *Jan. 11, 2022

(54) BLOOD ANALYSIS CARTRIDGE

(71) Applicant: King Abdulaziz University, Jeddah (SA)

(72) Inventors: Mazin A. Zamzami, Jeddah (SA); Hani Choudhry, Jeddah (SA); Samar Damiati, Jeddah (SA); Martin Peacock, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,492

(22) Filed: Jun. 18, 2021

(65) Prior Publication Data

US 2021/0308674 A1 Oct. 7, 2021

Related U.S. Application Data

(63) Continuation of application No. 16/502,615, filed on Jul. 3, 2019.

(51) Int. Cl.
B01L 3/00 (2006.01)
C12Q 1/48 (2006.01)
G01N 27/327 (2006.01)

(52) U.S. Cl.
CPC ..... *B01L 3/502715* (2013.01); *B01L 3/50273* (2013.01); *B01L 3/502761* (2013.01);
(Continued)

(58) Field of Classification Search
CPC .. B01L 3/502715; B01L 3/5027; B01L 3/502; B01L 3/50; B01L 3/50273;
(Continued)

(56) References Cited

U.S. PATENT DOCUMENTS 5,262,067 A * 11/1993 Wilk ............... B01D 39/00
210/506
5,460,974 A * 10/1995 Kozak ............... C12Q 1/60
422/412

(Continued)

FOREIGN PATENT DOCUMENTS

CN 105567786 A 5/2016
WO 2008/110019 A1 9/2008
(Continued)

OTHER PUBLICATIONS

Peng, Structural Basis of Substrate Recognition in Thiopurine S-Methyltransferase, Biochemistry. Jun. 10, 2008; 47(23): 6216-6225 (Year: 2008).*

(Continued)

*Primary Examiner* — Christine T Mui
(74) *Attorney, Agent, or Firm* — Oblon, McClelland, Maier & Neustadt, L.L.P.

(57) ABSTRACT

A test microfluidic strip or cartridge comprising a blood sample collection zone, red blood cell isolation zone, lysis zone, reagents mixing zone, and sensing zone for measuring the enzymatic activity thiopurine methyltransferase is disclosed. The test strip or cartridge is disclosed to be operably connected to a metering device comprising a processor, a display and a memory card.

4 Claims, 4 Drawing Sheets

(52) U.S. Cl.
CPC ........... *C12Q 1/48* (2013.01); *G01N 27/3272* (2013.01); *G01N 27/3276* (2013.01); *B01L 2200/16* (2013.01); *B01L 2300/025* (2013.01); *B01L 2300/0681* (2013.01); *B01L 2300/18* (2013.01); *B01L 2400/0406* (2013.01); *B01L 2400/0475* (2013.01)

(58) Field of Classification Search
CPC ........... B01L 3/502761; B01L 2200/16; B01L 2300/0681; B01L 2300/18; B01L 2400/0406; B01L 2400/0475
USPC ........................................ 422/502, 501, 500
See application file for complete search history.

(56) References Cited

U.S. PATENT DOCUMENTS

| | | | |
|---|---|---|---|
| 5,863,502 A * | 1/1999 | Southgate | B01J 19/0093 422/417 |
| 6,576,438 B2 | 6/2003 | Barstad | |
| 6,946,258 B2 | 9/2005 | Padhye et al. | |
| 7,727,737 B2 | 6/2010 | O'Brien et al. | |
| 8,703,069 B2 * | 4/2014 | Handique | C12Q 1/686 422/503 |
| 2006/0207891 A1 * | 9/2006 | Althaus | G01N 33/54373 205/787 |
| 2007/0106333 A1 | 5/2007 | Fernandex | |
| 2012/0282634 A1 * | 11/2012 | Hughes | G01N 33/558 435/7.25 |
| 2013/0022971 A1 | 1/2013 | Sanderson et al. | |

FOREIGN PATENT DOCUMENTS

| | | |
|---|---|---|
| WO | 2008/119190 A1 | 10/2008 |
| WO | 2017/106790 A1 | 6/2017 |
| WO | 2018/057647 A1 | 3/2018 |

OTHER PUBLICATIONS

Konstantou, et al. ; Dual-allele dipstick assay for genotyping single nucleotide polymorphisms by primer extension Reaction ; European Journal of Human Genetics 17 ; pp. 105-111 ; 2009 ; 7 Pages.

Chowdhury, et al. ; Microfluidic Platform for Single Nucleotide Polymorphism Genotyping of the Thiopurine S-Methyltransferase Gene to Evaluate Risk for Adverse Drug Events ; Journal of Molecular Diagnosis, vol. 9, No. 4 ; Sep. 2007 ; 9 Pages.

Marz, et al. ; Detection of thiopurine methyltransferase activity in lysed red blood cells by means of lab-on-a-chip surface enhanced Raman spectroscopy (LOC-SERS) ; Analytical and Bioanalytical Chemistry, vol. 400, issue 9 ; pp. 2755-2761 ; Jul. 2011 ; Abstract Only ; 1 Page.

Lien, et al. ; Miniaturization of molecular biological techniques for gene assay ; Analyst, Issue 7 ; 2010 ; Abstract Only ; 2 Pages.

Shaw, et al. ; Microsystems for personalized biomolecular Diagnostics; Eng. Life Sci., 11, No. 2 ; pp. 121-132 ; 2011 ; 12 Pages.

* cited by examiner

BLOOD ANALYSIS CARTRIDGE

CROSS-REFERENCE TO RELATED APPLICATIONS

The present application is a Continuation of Ser. No. 16/502,615, pending, having a filing date of Jul. 3, 2019.

BACKGROUND OF THE INVENTION

Technical Field

The invention relates to a system comprising a disposable strip or cartridge for rapid determination of thiopurine S-methyltransferase (TPMT) activity in biological fluids, and a method of using the system to detect and/or determine thiopurine S-methyltransferase (TPMT) activity in a subject.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Acute lymphocytic leukemia (ALL) is the most common malignant disease in children (about 80% of all cases) and it is the second most common leukemia in adults with over 6500 cases per year in the United States [Terwilliger et al. Acute lymphoblastic leukemia: a comprehensive review and 2017 update. Blood Cancer J, 2017. 7(6): p. e577]. Childhood cancers constitute about 7% of all cancers among Saudis, and Lymphoblastic leukemia is considered the primary cause of cancer deaths in children and young people in Saudi Arabia [Stiller et al. Geographic and ethnic variations in the incidence of childhood cancer. Br Med Bull, 1996. 52(4): p. 682-703; and McLeod et al. The thiopurine S-methyltransferase gene locus: implications for clinical pharmacogenomics. Pharmacogenomics, 2002. 3(1): p. 89-98]. In the past three decades progress in diagnosing, managing, and treating ALL has led to a dramatic improvement in survival rates around the world. Currently, it is estimated that the survival rate is more than 85% [Pui et al. Improved outcome for children with acute lymphoblastic leukemia: results of Total Therapy Study XIIIB at St Jude Children's Research Hospital. Blood, 2004. 104(9): p. 2690-6; and Siegel et al. Cancer statistics, 2011: the impact of eliminating socioeconomic and racial disparities on premature cancer deaths. CA Cancer J Clin, 2011. 61(4): p. 212-36].

Thiopurine (TP) and its derivatives are used as adjuvant therapies to prevent organ transplant rejection, as well as in the treatment of Crohn's disease (a bowel disorder), Behçet's disease, a variety of skin conditions, and rheumatic and neurological disorders in which the immune system is believed to play a role. Although thiopurine is an effective drug and relatively inexpensive, it has serious side effects including death in some cases [Park et al. Updated treatment strategies for intestinal Behcet's disease. Korean J Intern Med, 2018. 33(1): p. 1-19; and Wiseman, A. C. Immunosuppressive Medications. Clin J Am Soc Nephrol, 2016. 11(2): p. 332-43].

A major chemotherapy component of ALL treatment protocols is the use of antimetabolites, in particular during maintenance therapy. Thiopurine antimetabolite derivatives such as 6-mercaptopurine (6-MP) and 6-thioguandine (6-TG) are cytotoxic and immunosuppressant agents commonly employed in a number of hematological malignancies including ALL and Acute Myeloid Leukemia (AML), cancer, organ transplant and autoimmune disease. They are highly active antimetabolite agent for the treatment of ALL, and are extensively used in current therapeutic protocols worldwide. For example, 6-MP is a critical component of successful ALL maintenance therapy, activated via the de novo purine synthesis (DNPS) inhibition. Several enzymes in the purine salvage pathway are involved in the metabolism of 6-MP (FIG. 1). In particular, hypoxanthine guanine phosphoribosyl transferase (HPRT) in the anabolic pathway modulates 6-thioguanine nucleotides (6-TGN) homeostasis; and TPMT in the catabolic pathway converts 6-MP to 6-methylmercaptopurine (6-MMP) [Weinshilboum, R. Thiopurine pharmacogenetics: clinical and molecular studies of thiopurine methyltransferase. Drug Metab Dispos, 2001. 29(4 Pt 2): p. 601-5; and Schwab et al. Pharmacokinetic considerations in the treatment of inflammatory bowel disease. Clin Pharmacokinet, 2001. 40(10): p. 723-51].

FIG. 1 shows the role TPMT in the metabolic pathway of thiopurine. Azathioprine is an anticancer and immune suppressive drug, which is converted non-enzymatically to 6-mercaptopurine (6-MP). Both 6-MP and 6-thioguanine (6-TG) are salvaged by hypoxanthine-guanine phosphoribosyltransferase (HPRT) to 6-thioinosine 5'-monophosohate (6-TIMP) and 6-thioguanosine monophosphate (6-TGMP), respectively. Also, thiopurine S-methyltransferase (TPMT) catalyzes the conversion of 6-MP and 6-TG to S-methylmercaptopurine (6-MMP) and S-6-methylthioguanine (6-MTG), respectively. In addition, xanthine oxidase converts 6-MP to 6-thiouric acid (6-TUA). Similarly, 6-TG is converted to 6-TUA via thioxanthine by the actions of guanase and XO, respectively. 6-TIMP is either methylated to 6-methylmercaptopurine ribonucleotide (6-MTIMP) by the action of TPMT or phosphorylated to or 6-thioinosine diphosphate (6-TIDP) and 6-thioinosine triphosphate (6-TITP) by monophosphate kinase (MPK) and diphosphate kinase (DPK), respectively. Inosine triphosphate pyrophosphatase (ITPase) catalyzes the conversion of 6-TITP back to 6-TIMP. If ITPase activity is deficient 6-TITP accumulates. Inosine monophosphate dehydrogenase (IMPD) catalyzes the formation of 6-thioxanthine monophosphate (6-TGMP). Guanosine monophosphate synthetase catalyzed the formation 6-thioguanosine monophosphate (6-TGMP). Finally, TPMT catalyzes the methylation of 6-TGMP to 6-methylguanosine monophosphate (6-MTGMP).

About 89% of Caucasians and African Americans have high TPMT activity in the blood, whereas only about 10% have intermediate activity, and less than 1% have little or no activity. Community surveys have shown that one out of every 300 people has no TPMT activity and nearly 11% of people in the community have low activity of the enzyme.

Patients with low or no activity of TPMT are at high risk of severe intoxication when treated with thiopurine compounds. Thus, determination of TPMT activity in a patent prior and during treatment with thiopurine compound is necessary to determine the course of treatment and appropriate dose. Such a dose would maintain a balance between the competitive pathways of the thiopurine compound to convert a sufficient portion of the thiopurine compound to the nucleotide triphosphate derivative to be incorporated into the DNA of the cancer cells leading to their death without causing significant harm to the bone marrow of the patient [Lennard, L. Implementation of TPMT testing. Br J Clin Pharmacol, 2014. 77(4): p. 704-14; and Gisbert et al. Thiopurine methyltransferase (TPMT) activity and adverse effects of azathioprine in inflammatory bowel disease: long-term follow-up study of 394 patients. Am J Gastroenterol, 2006. 101(12): p. 2769-76.].

In the late 1970s, the activity of TPMT was first assessed and considered in different human tissues with the aim of identifying the biochemical pathways responsible for the differences observed in drug toxicity and/or efficacy in patients treated with thiopurine. In 1980, Weinshilboum and Sladek performed a TPMT activity assay for large population samples, which indicate that the TPMT level in red blood cells was controlled by common polymorphism [Murugesan et al. Thiopurine S-methyltransferase alleles, TPMT (*)2, (*)3B and (*)3C, and genotype frequencies in an Indian population. Exp Ther Med, 2010. 1(1): p. 121-127.]. Two alleles have been identified and designated TPMT(H) and TPMT(L) for alleles having high and low TPMT activity, respectively. It has been found that approximately 90% of individuals are homozygous of the wild-type TPMTH allele, and TPMT activity defines normal enzymatic activity. On the other hand, about 0.3% of individuals are homozygous for the TPMTL allele (TPMTL/TPMTL), and either lack or have very little TPMT activity [Weinshilboum, R Thiopurine pharmacogenetics: clinical and molecular studies of thiopurine methyltransferase. Drug Metab Dispos, 29(4 Pt 2): p. 601-5 (2001)].

Human TPMT contains 245 amino acids having a molecular weight of 28 kDa. TPMT gene is localized to chromosome 6p22.3 and encoded by 34 kb bases. TPMT gene contains 10 exons and 9 introns [Schwab et al. Pharmacokinetic considerations in the treatment of inflammatory bowel disease. Clin Pharmacokinet, 2001. 40(10): p. 723-51]. Up to now, 23 alleles of the TPMT gene have been identified accounting for 80-95% of TPMT activity deficiency [Lennard, L. Implementation of TPMT testing. Br J Clin Pharmacol, 2014. 77(4): p. 704-14; and Gisbert et al. TPMT activity and adverse effects of azathioprine in inflammatory bowel disease: long-term follow-up study of 394 patients. Am J Gastroenterol, 2006. 101(12): p. 2769-76.]. TPMT homozygous and heterozygous are most likely of developing severe myelosuppression due to intracellular accumulation of active toxic metabolite of 6-TGN as shown in FIG. 1 [Murugesan et al. Thiopurine methyltransferase alleles, TPMT(*)2, (*)3B and (*)3C, and genotype frequencies in an Indian population. Exp Ther Med, 2010. 1(1): p. 121-127; and Relling et al. Clinical pharmacogenetics implementation consortium guidelines for thiopurine methyltransferase genotype and thiopurine dosing: 2013 update. Clin Pharmacol Ther, 2013. 93(4): p. 324-5]. TPMT*3A and *3C seem to be common alleles associated with diminished enzyme activity. In addition, TPMT deficient patients are more at risk to develop a brain tumor (Astrocytoma) as a late secondary cancer complication than those who had high or normal TPMT [42.9% versus 15.8% 10-year cumulative incidence, respectively (Relling et al.)].

TABLE 1

Percent prevalence of TPMT*2, TPMT*3A, TPMT*3B, and TPMT*3B in different populations

| Ethnicity of Participants | No of Participants | TPMT*2 (%) | TPMT*3A (%) | TPMT*3B (%) | TPMT*3C (%) |
|---|---|---|---|---|---|
| African American | 326 | 0.40 | 0.8 | N/D | 2.4 |
| Caucasian American | 282 | 0.20 | 3.2 | N/D | 0.2 |
| Brazilian | 306 | 0.8 | 2.0 | N/D | 2.5 |
| Kenya | 101 | 0.00 | 0.0 | 0.00 | 5.4 |
| British Caucasian | 199 | 0.5 | 4.5 | 0.00 | 0.30 |
| Egyptian | 200 | 0.00 | 0.30 | 0.00 | 1.30 |
| French Caucasian | 469 | 3.00 | 0.7 | N/D | 0.4 |
| Italian | 103 | 0.50 | 3.9 | N/D | 1.00 |
| Swedish | 800 | 0.10 | 3.8 | 0.10 | 0.40 |
| South East Asia | 300 | 0.00 | 0.00 | 0.00 | 1.00 |

The results in Table 1 clearly show that polymorphism in the TPMT varies in different ethnic groups. East and West Africans and south East Asians have significant prevalence of the TPMT3*C allele and little or no prevalence of TPMT*3A. In contrast, European populations have a modest prevalence of the TPMT3*C allele and significant prevalence of TPMT*3A. In the French Caucasian population, TPMT*2 is the most prevalent allele. The results of Table 1 is consistent with the idea that the allelic variants of TPMT are responsible for the variation of the observed toxicity and efficacy in patients treated with 6-MP [McLeod et al. The thiopurine S-methyltransferase gene locus: implications for clinical pharmacogenomics. Pharmacogenomics, 2002. 3(1): p. 89-98; and Murugesan et al. Thiopurine S-methyltransferase alleles, TPMT(*)2, (*)3B and (*)3C, and genotype frequencies in an Indian population. Exp Ther Med, 2010. 1(1): p. 121-127.].

In a clinical setting, screening patents for TPMT activity is expected to improve the outcome of chemotherapy treatment involving the use of thiopurine compounds, and lower the coast of treatment. Significant dose reduction and treatment protocol modification are required for patents with low TPMT activity to minimize the occurrence of grade 4 toxicity of bone marrow suppression [Relling et al. Clinical pharmacogenetics implementation consortium guidelines for thiopurine methyltransferase genotype and thiopurine dosing: 2013 update. Clin Pharmacol Ther, 2013. 93(4): p. 324-5; and Relling et al. Clinical Pharmacogenetics Implementation Consortium guidelines for thiopurine methyltransferase genotype and thiopurine dosing. Clin Pharmacol Ther, 2011 98 (3) 387-391]. For instance, the treatment dose can be reduced to approximately 90% for patients with the TPMT enzyme deficiency, and a 40% dose reduction may be required for patients with the low TPMT activity of ALL pediatric patients as per recommendation of Children Oncology Group [Group, C.s.O., AALL0232: High Risk B-precursor Acute Lymphoblastic Leukemia (ALL): A Phase III Group-Wide Study. 2008].

U.S. Pat. No. 6,576,438B2 discloses a method for determining TPMT activity comprising contacting a sample of red blood cell lysate with 6-thioguanine, acid precipitating the protein in the sample, removing the precipitate, and detecting the methylated product by fluorescence and/or HPLC. While the method may be effective in determining the TPMT activity, it is laborious containing several processing steps each of which has the potential of introducing error in the measurement.

U.S. Pat. No. 6,946,258 discloses a rapid immunoassay for measuring TPMT activity in a sample. The method requires raising an antibody specific for binding 6-methylmercaptopurine and coating ELISA plate with a protein-6-MP conjugate which are costly. Once the reagents are prepared, the method comprises contacting a sample containing the enzyme with the plate and detecting an optical signal at 450 nm. The method is accurate and amenable to automation, but it requires laboratory equipment and would be difficult to carry out in a clinical setting.

US2013/0022971A discloses a method for predicting a patient's risk of an adverse effect or tolerance to a 6-mercaptopurin drug by genotyping a patient at a polymorphic site in at least one gene selected from the group consisting of xanthine dehydrogenase gene, molybdenum cofactor sulfurase gene, and aldehyde oxidase gene. The method contains several step including isolating DNA, PCR, and the use short nucleotide probe for detection. It laborious, time consuming and cannot be carried out in a clinical setting.

A label-free biosensor is highly desirable for efficient detection of target analytes and has recently attracted considerable attention. Designing a functionalized biosensor with good biocompatibility for detection of target analytes is a challenging task that must have high selectivity and sensitivity. Currently, several biosensor techniques are being exploited to detect a specific biomarker, such as acoustic [Damiati et al. Bioinspired detection sensor based on functional nanostructures of S-proteins to target the folate receptors in breast cancer cells. Sensors and Actuators B: Chemical, 2018. 267: p. 224-230; and Damiati et al. Acoustic and hybrid 3D-printed electrochemical biosensors for the real-time immunodetection of liver cancer cells (HepG2). Biosens Bioelectron, 2017. 94: p. 500-506.], electrochemical [Islam, K., et al., Development of a Label-Free Immunosensor for Clusterin Detection as an Alzheimer's Biomarker. Sensors (Basel), 2018. 18(1)], field-effect transistor [Haslam et al. Label-Free Sensors Based on Graphene Field-Effect Transistors for the Detection of Human Chorionic Gonadotropin Cancer Risk Biomarker. Diagnostics, 2018. 8(1): p. 5], and surface plasmon resonance [Schrems et al. Liposome fusion on proteinaceous S-layer lattices triggered via[small beta]-diketone ligand-europium(iii) complex formation. Soft Matter, 2011. 7(12): p. 5514-5518.]. While each technique offers several advantages, each has drawbacks. Electrochemical sensors are preferred because they are accessible and affordable at point-of-care. Several advantages are provided by electrochemical methods such as speed, simplicity, low cost, using a small amount of reagent and sample volume, high efficiency, and selectivity to detect specific analyte. In addition, they are small in size, and can be integrated into a compact systems enabling sampling and microfluidic handling [Damiati, S., et al., Cell-Free Approaches in Synthetic Biology Utilizing Microfluidics. Genes (Basel), 2018. 9(3), and Damiati, S., et al., Embedded Disposable Functionalized Electrochemical Biosensor with a 3D-Printed Flow Cell for Detection of Hepatic Oval Cells (HOCs). Genes (Basel), 2018. 9(2))(DOI10.3390/genes9020089)]. Embedding electrochemical biosensors in a microfluidic system allows performing of chemical and biomedical analysis and enables recognition of analyte in real-time and in situ monitoring.

It is therefore one object of the present disclosure to provide a compact device to be used in clinical setting comprising a test strip or cartridge to measure TPMT activity using a whole blood drop.

BRIEF SUMMARY OF THE INVENTION

According to a first aspect, the present disclosure relates to a microfluidic test strip or cartridge for measuring the activity of thiopurine S-methyltransferase (TPMT) in a blood sample comprising a blood sample collection zone, a red blood cell isolation zone, a lysis zone, a reagent mixing zone, and a sensing zone, wherein the biological fluid passes from one zone to another by capillary action and/or microfluidic pump, and wherein the red blood cell isolation zone comprises a filtration system for separating red blood cells from plasma, and the system comprises (i) a series of filters that retains red blood cells and remove plasma and other blood cells components ranging in diameter from 9 to 30 μm and 0.1 to <4 μm, or (ii) a cross-flow filtration system that separates red blood cells from whole blood.

In a preferred embodiment, the flow of blood from the collection zone through filtration system to the sensing zone is driven by capillary forces.

In another preferred embodiment, the lysis zone comprising a cell lysing agent selected from the group consisting of a detergent, an ammonium salt, and combination thereof.

In a more preferred embodiment, the lysing agent is a detergent selected from the group consisting of Triton X-100, Triton X-114, NP-40, Brij-35, Brij-58, Tween 20, Tween 80, octyl glucoside, octyl thioglucoside, sodium dodecyl sulfate (SDS), 3-[(3-cholamidopropyl)dimethylammonio]-1-propanesulfonate (CHAPS), and 3-[(3-cholamidopropyl)dimethylammonio]-2-hydroxy-1-propanesulfonate (CHAPSO).

In the most preferred embodiment, the lysing agent comprises ammonium salt has the chemical formula $R_1N^+(R_2)_3X^-$ where R1 and R2 are independently H or alkyl group of 4 to 18 carbon atom, and X is selected from the group consisting of chloride, bromide, fluoride, acetate, phosphate.

In another preferred embodiment, the reagents mixing zone comprises a mercaptopurine compound, S-adenosyl-L-methionine, and optionally buffer having a pH in the range of 6.0 to 8.0.

In a more preferred embodiment, the mercaptopurine compound is 6-mercaptopurine or 6-thioguanine.

In another preferred embodiment, the sensing zone comprising an electrochemical sensing system.

In a more preferred embodiment, the electrochemical sensing system measures change in concentration of one or more of a mercaptopurine compound, a methylated mercaptopurine compound, S-adenosyl-L-methionine, S-adenosyl-homocysteine, and hydrogen ion.

In another preferred embodiment, the sensing zone comprises an optical detection system.

In a more preferred embodiment, the optical detection system detects change in UV/vis or fluorescence spectra.

In another preferred embodiment, the test strip or cartridge comprises a series of micropumps that can drive blood when present in the strip or cartridge through the filtration system, the lysis zone, the mixing zone reagents, and to the sensing zone.

In another preferred embodiment, the test strip or cartridge comprises cross flow filtration system that separates red blood cells from whole blood.

In another preferred embodiment, the test strip or cartridge further comprises a filter between the lysis zone and the reagent mixing zone to separate lysed red blood cells from intact white blood cells.

In another preferred embodiment, the blood sample collection zone of test strip or cartridge comprises at least one anti-coagulant.

A second aspect of the invention is directed to a device for measuring the activity of thiopurine S-methyltransferase (TPMT) in a biological fluid comprising:

a meter comprising a display, a signal processor, and a memory card, and the test strip or cartridge disclosed herein, wherein the device has temperature controlled compartment for the sensing zone.

In a preferred embodiment, the sensing zone of the device is operatively connected to the processor and the display.

A third aspect of the invention is directed to a method for detecting and measuring TPMT activity in blood comprising contacting a blood sample from a subject with the device disclosed herein and detect a signal generated in the sensing zone due to the methylation of a thiopurine compound catalyzed by the action of TPMT.

In a preferred embodiment of the method, the thiopurine compound of the method is 6-mercaptopurine or 6-thioguanine.

In another preferred embodiment of the method, the signal is an electrochemical signal.

In another preferred embodiment, the subject is a mammal, preferably human.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
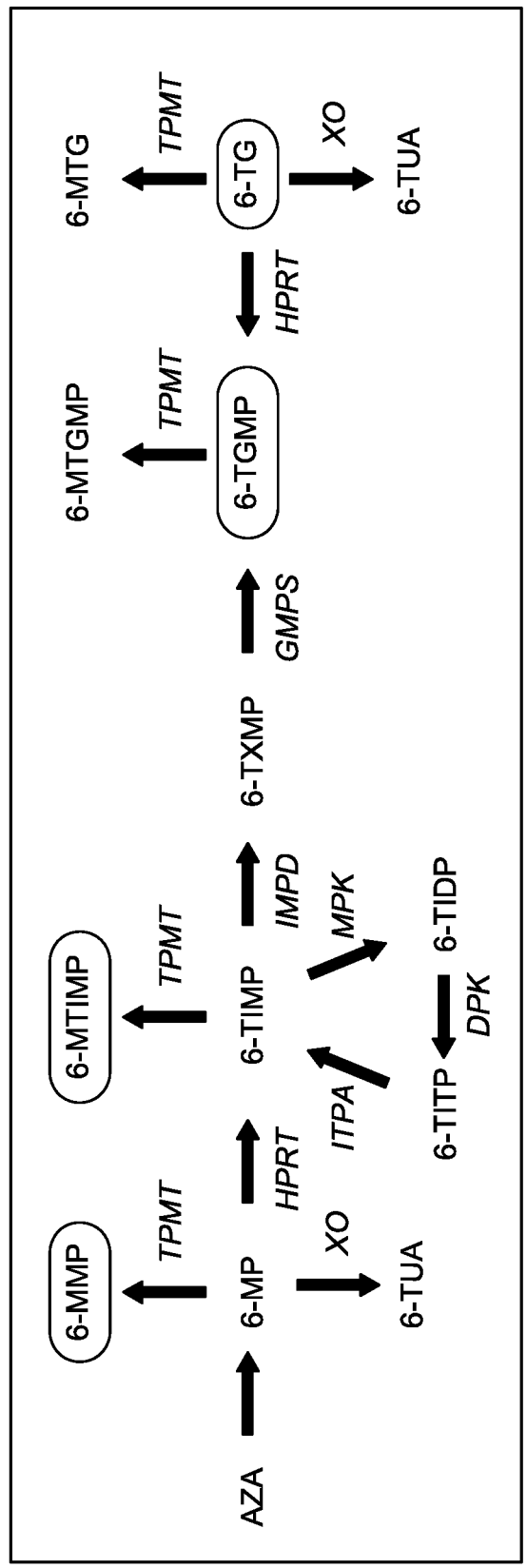
FIG. 1 shows the metabolic pathway of thiopurine.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

The terminology used herein is for the purpose of describing particular embodiments only and is not intended to be limiting of the invention.

The headings such as "Background" and "Summary", and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

The terms "comprises" and/or "comprising," when used in this specification, specify the presence of stated features, steps, operations, elements, and/or components, but do not preclude the presence or addition of one or more other features, steps, operations, elements, components, and/or groups thereof.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Although the terms "first" and "second" may be used herein to describe various features/elements including steps, said features/elements should not be limited by such terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Disclosure of values and ranges of values for specific parameters (such as temperatures, molecular weights, weight percentages, etc.) are not exclusive of other values and ranges of values useful herein. Two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients. Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

As used herein, the phrase "operably linked" is intended to mean that two or more elements are physically connected together to perform certain task such as a test strip and a metering device so the test strip prepare the sample for measurement and produces a signal, and the meter process the signal and display the results.

According to a first aspect, the present disclosure relates to a microfluidic test strip or cartridge for measuring the activity of thiopurine S-methyltransferase (TPMT) in a blood sample comprising:
   a blood sample collection zone,
   a red blood cells isolation zone,
   a lysis zone,
   a reagents mixing zone, and
   a sensing zone,
   wherein the biological fluid passes from one zone to another by capillary action and/or microfluidic pump, and
   wherein the red blood cell isolation zone comprises a filtration system for separating red blood cells from plasma, and the system comprises (i) a series of filters that retains red blood cells and remove plasma and other blood cells components ranging in diameter from 9 to 30 µm and 0.1 to <4 µm, or (ii) a cross-flow filtration system that separates red blood cells from whole blood.

The test strip/cartridge is intended to be used in conjunction with an electronic meter such as that described below to measure and monitor TPMT activity at home or at a point of care. The term "point-of-care" as used herein is defined to mean a location on or near a site of patient care where medical testing and/or treatment can be performed. For example, locations for point-of-care may include but are not limited to, hospitals, patient homes, the home of a friend or relative, a physician's office, or a site of an emergency. The electronic meter provides an immediate result to the patent and/or the care provider immediately such as that used in glucose monitoring systems.

The strip or cartridge may be disposable or reusable after flushing out the old sample with saline solution and recharging the strip or cartridge with reagents. The volume of the blood sample needed for measuring the TPMT activity can vary depending on the configuration and the design of the strip or cartridge. In some embodiment, the sample volume is in the range of 1.0 µL to 100 preferably in the range of 2.0 µL to 50 more preferably in the range of 3.0 µL to 20 and most preferably in the range of 5.0 µL to 10 µL. In some other embodiment, the sample volume is in the range of 100 µL mL to 900 preferably in the range of 200 µL to 700 more preferably in the range of 300 µL to 600 and most preferably in the range of 400 µL to 500 µL. Thus, the path from the sample collection zone to the detection zone must accommodate the entire sample volume to produce reliable and reproducible results. Depending on the function of each zone and the type of filters used, the path length and volume of each zone may vary. In some embodiments, the red blood cell isolation zone may have only one filter to remove the larger white blood cells. In other embodiments, it may have two filters to remove the larger white blood cells and the small platelets.

The different zones are connected in such a way the fluids move from one zone to another in sequence so that the sample is processed to produce purified lysed red blood cells when the lysed red blood cells reach the sensing zone. The sample collection zone has the largest volume as it receives the unprocessed whole blood sample. In some embodiments, the sample collection zone/void has a volume in the range of 100 µL mL to 900 preferably in the range of 200 µL to 700 more preferably in the range of 300 µL to 600 and most preferably in the range of 400 µL to 500 µL. In other embodiments, the sample collection zone has a volume in the range of 1.0 µL to 100 preferably in the range of 2.0 µL to 50 more preferably in the range of 3.0 µL to 20 and most preferably in the range of 5.0 to 10 µL.

The red blood cell isolation zone lies between the sample collection zone and the lyses zone and contains one or more filters to isolate the red blood cells. In some embodiment, a fine filter to remove the large white blood cells larger than 8 µm followed by a second filter to remove the plasma and platelet of less than 4 µm leaving behind the red blood cells. In some embodiment, the total volume of the red blood cell isolation zone/void is in the range 20 µL to 400 preferably in the range 30 µL to 300 more preferably in the range of 40 µL to 200 and most preferably in the range of 50 µL to 100 µL. In some other embodiment, the total volume of the zone is in the range of 1 µL to 20 preferably in the range of 1 µL to 15 µL, more preferably in the range of 1 µL to 10 µL, and most preferably in the range 1 µL to 2 µL.

The lysis zone/void is connected to the blood cells isolation zone and the reagent mixing zone and contains the lysing reagent. In some embodiments, it has a volume in the range of 20 µL to 50 µL, preferably in the range of 20 µL to 40 µL, more preferably in the range of 20 µL 30 µL, and most preferably in the range of 20 µL to 25 µL. In some other embodiments, the lysing zone has a volume in the range of 1 µL to 5 µL, preferably in the range of 1 µL to 3 µL, and more preferably about 2 µL.

The reagents mixing zone/void is connected to the lysis zone and the sensing zone. In some embodiment, it has a volume of 10 µL to 30 µL and preferably in the range of 15 µL to 20 µL. In some other embodiments, reagents mixing zone has a volume in the range of 1 µL to 5 µL, preferably in the range of 1 µL to 3 µL, and more preferably about 1 µL to 2 µL.

The sensing zone/void is connected to the reagent mixing zone and contains a vent. The volume of the sensing zone is sufficient to contain a sample sufficient to produce measurable signal. In some embodiments, the volume is in the range 5 µL to 15 µL, more preferably about 10 µL. In some other embodiment, the volume of the zone is in the range of 1 µL to 4 µL, and more preferably about 2 µL. The wall of the sensing zone should be transparent to light if optical detection is desired. Alternatively, an electrode system is embedded in the sensing zone.

The blood samples may be obtained from patients by any method in the art. Conventional methods require a needle or lancet to venipuncture or finger stick or skin stab to obtain the blood needed for testing. Needleless blood collection has been recently developed which obviates some the drawbacks of the conventional methods such as time and cost to have blood professionally collected at hospital, doctor's office or other health facility, resistance or non-compliance by patients afraid of needles (trypanophobia) or skin stabs, fainting, lightheadedness, bruising around the anatomical site of collection, hematoma, phlebitis or swelling of a vein after blood collection, and excessive bleeding by patients taking blood thinning medicines or agents such as aspirin or warfarin. In contrast to conventional venipuncture and fingers sticking, needleless blood collection obtains blood from a capillary bed close to the surface of a skin under a gentle vacuum. Such needle-less blood collection techniques are described by HemoLink™ (World Wide Web.tassoinc.com/vision/), US 2016/0174888 A1, or by U.S. 2015/0342509, "Needle-free Blood Draw" both of which are incorporated by reference in their entirety.

The term "blood components" describes components that may be found in a sample of blood. For example, the blood components may include, but are not limited to white blood cells, also known as leukocytes, red blood cells, also known as erythrocytes, platelets, plasma, and bacteria. Plasma is usually produced by collecting whole blood in tubes that are treated with an anticoagulant so that the blood does not clot. The cells are then removed by centrifugation and the supernatant, designated plasma, carefully removed from the resulting cell pellet using a Pasteur pipette. Serum is the liquid fraction of whole blood that is collected after the blood is allowed to clot. Generally clotting takes 15-30 mins. The clot may be removed by centrifugation and the resulting supernatant, designated serum, is removed using a Pasteur pipette.

Figure 2:
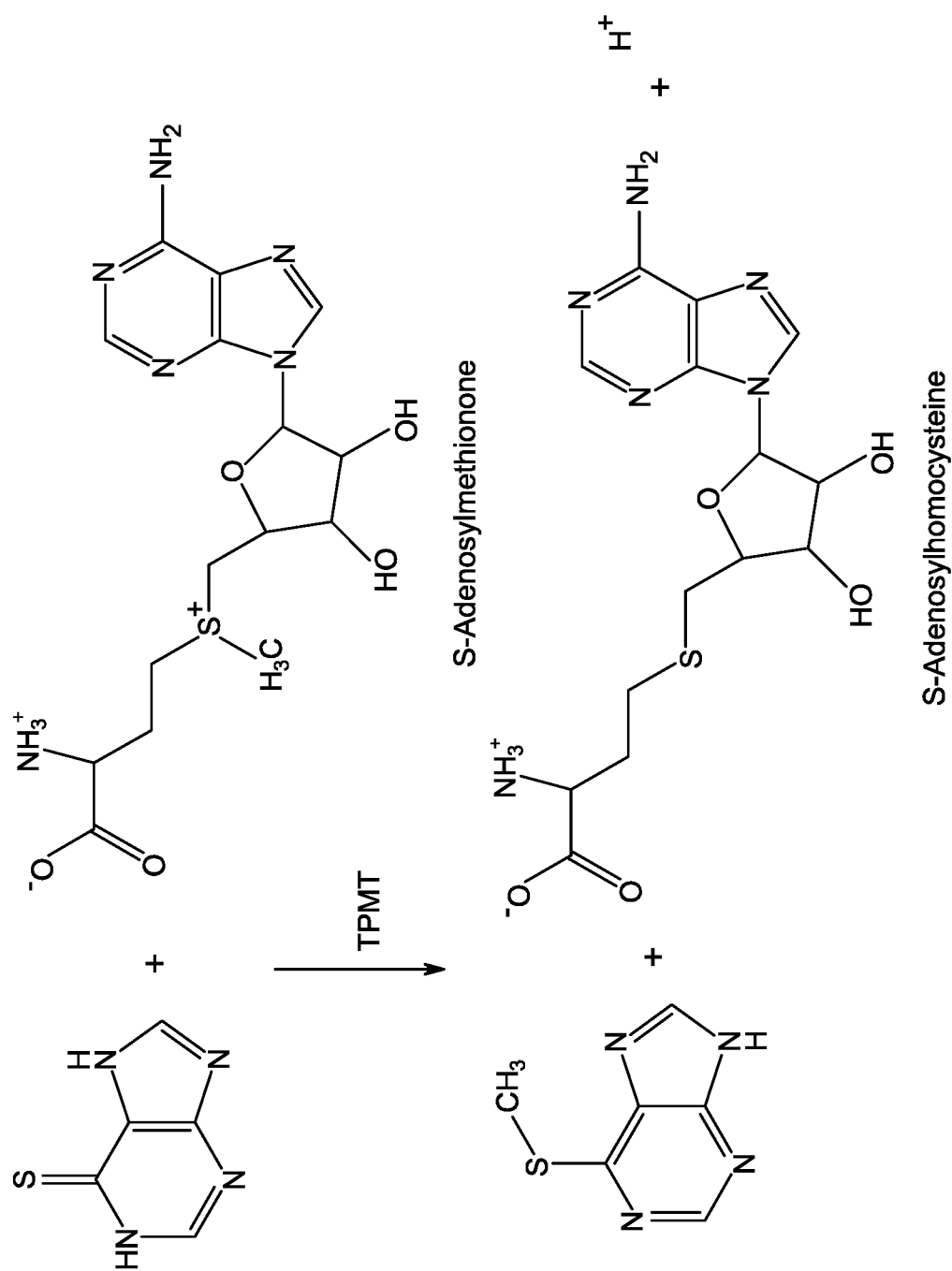
FIG. 2 shows 6-mercaptopurine methylation catalyzed by TPMT.

TPMT is located inside red blood cells and catalyzes the transfer of a methyl group from S-adenosylmethionine (SAM) to the sulfur atom of a thiopurine compound such as 6 MP or 6-TG to produce a thiomethylated purine compound and S-adenosylhomocysteine (SAH). An example reaction catalyzed by TPMT is shown in FIG. 2. The microfluidic test strip or cartridge is designed in such a way to isolate, purify, and lyse the red blood cells from whole blood sample prior to contacting the red blood cells with either a thiopurine substrate or 5-adenosylmethionine.

Figure 3:
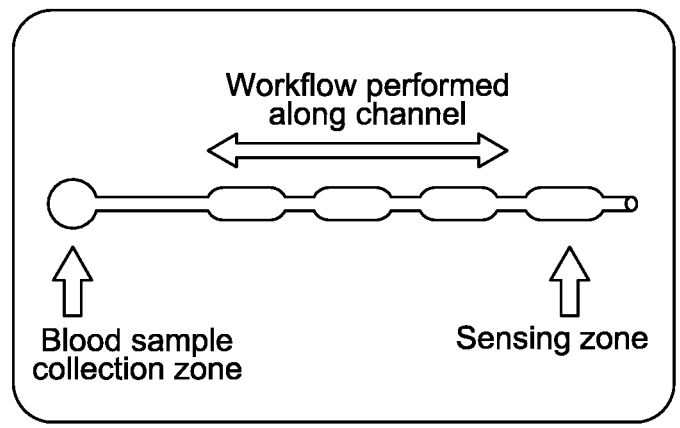
FIG. 3 shows an embodiment of the layout of the disposable strip or cartridge.
Figure 4:
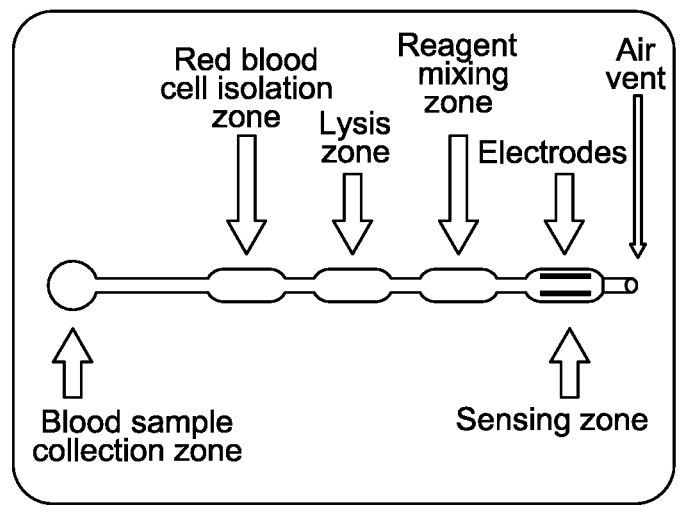
FIG. 4 show an embodiment of the different zones of the disposable strip or cartridge and their functions.

FIGS. 2 and 3 show a diagram intended to illustrate an embodiment of the microfluidic test strip or cartridge in linear horizontal configuration. While the linear horizontal configuration shown in the Figures is one of the preferred embodiments, it is not intended to limit the microfluidic test strip/cartridge of the invention to the linear configuration. Other configuration includes, but not limited to vertical, tilted, angular, circular, and ladder-type configurations. Thus, any type of configuration is within the scope of the invention as long as the blood sample flows from the blood collection zone of the test strip/cartridge to the sensing zone.

The effects of physical laws change within the microfluidic domain. As an example, volumetric forces, such as weight or inertia, often become negligible, whereas surface forces can dominate fluid behavior. Most micropumps rely on principles of micro-actuation which can be scaled up only to a certain size. Micropumps are grouped into mechanical and non-mechanical devices. Mechanical systems contain moving parts that are usually actuation and valve membranes or flaps. A driving force for a mechanical system can be generated using piezoelectric, electrostatic, thermo-pneumatic, pneumatic or magnetic effects. In contrast, non-mechanical pumps function with electro-hydrodynamic, electro-osmotic, electrochemical or ultrasonic flow generation. Non-mechanical pumps that are chemically powered may have nanomotors fixed to surfaces to facilitate a chemical reaction powering the pump. A wide variety of pumping systems exist ranging from enzyme-based pumps to those using an organic photocatalyst or those using a metal catalyst. These pumps generate flow through a number of different mechanisms including self-diffusiophoresis, electrophoresis, bubble propulsion and the generation of density gradients.

Mechanical pumps include diaphragm micropump and peristaltic micropump. A diaphragm micropump uses the repeated actuation of a diaphragm to drive a fluid. The membrane is positioned above a main pump valve, which is centered between inlet and outlet microvalves. When the membrane is deflected upwards through some driving force, fluid is pulled into the inlet valve into the main pump valve. The membrane is then lowered, expelling the fluid through the outlet valve. This process is repeated to pump fluid continuously. In a peristaltic micropump, a micropump has at least three microvalves in series. These three valves are opened and dosed sequentially in order to pull fluid from the inlet to the outlet in a process known as peristalsis.

Several non-mechanical micropumps are known in the prior art including valveless micropump, capillary pump, and chemical powered pump. In valveless pumps, static valves are defined as valves which have fixed geometry without any moving parts. These valves provide flow rectification through addition of energy (active) or inducing desired flow behavior by fluid inertia (passive). Two most common types of static geometry passive valves are Diffuser-Nozzle Elements and Tesla valves. Micropumps having nozzle-diffuser elements as flow rectification device are commonly known as valveless micropumps. In microfluidics, capillary pumping plays an important role because the pumping action does not require external actuation power. Glass capillaries and porous media, including nitrocellulose paper and synthetic paper, can be integrated into microfluidic chips. Capillary pumping is widely used in lateral flow testing. Recently, novel capillary pumps, with a constant pumping flow rate independent of the liquid viscosity and surface energy, were developed, which have a significant advantage over the traditional capillary pump (of which the flow behavior is Washburn behavior, namely the flow rate is not constant) because their performance does not depend on the sample viscosity. Chemically powered non-mechanical pumps have been fabricated by affixing nanomotors to surfaces, driving fluid flow through chemical reactions. A wide variety of pumping systems exist including biological enzyme based pumps, organic photocatalyst pumps, and metal catalyst pumps. These pumps generate flow through a number of different mechanisms including self-diffusiophoresis, electrophoresis, bubble propulsion and the generation of density gradients.

In microfluidics, capillary pumping plays an important role because the pumping action does not require external actuation. Glass capillaries and porous media, including nitrocellulose paper and synthetic paper, can be integrated into microfluidic test strip or cartridge. Capillary pumping is widely used in lateral flow testing and can be used in methods that separate a liquid from solid components in a biological sample. Capillary pumps, with a constant pumping flow rate independent of the liquid viscosity, have been developed, which have a significant advantage over the traditional capillary pump because their performance does not depend on the sample viscosity.

Miniaturized devices, obtained with micromachining techniques, into which a blood sample is introduced, may be used to detect the activity of TPMT. Some of these microfluidic devices, generically known as "Lab-On-Chip" or "Lab-On-a-chip" (LOC) or "Micro Total Analysis Systems" (µTAS), are known as "microfluidic devices" because they integrate one or more miniaturized hydraulic components, such as paths, passages, valves, filters, and obstacles, which have at least one characteristic such as length, width, height, thickness, section of passage, etc., of less than 1 mm. For example, an intake for a biological sample, pathway between an intake and a filter, or pathway from a filter to a detecting region, or a detecting region may be dimensioned to have a height, width, or length of 25, 50, 100, 200, 250, 300, 350, 400, 500, 600, 700, 800, 900 or ≤1,000 µm or any intermediate value or subrange within this range. In other embodiments a microfluidic chip may comprise smaller or larger dimensions, such as 1, 2, 3, 4, 5 or more millimeters, so long as the fluid that is received, conducted, processed or detected can move through the strip or cartridge, for example, by capillary action or by microfluidic pumping.

In some embodiments, the microfluidic path connecting the different zones may comprise smaller or larger dimensions, such as 1, 2, 3, 4, 5 or more millimeters, so long as the fluid that is received, conducted, processed or detected can move through the strip or cartridge by capillary action or microfluidic pumping. The aspect of height-width ratio is an important parameter for successfully injection molding micro-channels. Tall and thin channels are usually preferred for fluidic functionality, for example, channels having a height to width ratio of >1:1, 1.5: 1, 2:1, 3:1, or 4:1. To use gravitational force in the direction of fluid flow, microfluidic channels can be designed with shorter and wider channels as microchannel design influences the effects of gravity and/or capillary forces.

Designing a channel that utilizes a combination of capillary and gravity forces can be accomplished by changing the geometry of the channel, properties of the fluids, and device materials. The Bond number can be used to design these channels from the Equation: $Bo=\Delta\rho g L^2/\sigma$ where $\Delta\rho$ is the difference in fluidic density between the fluid flowing in the channel and the fluid surrounding it, g is the gravitational constant, L is the characteristic length of the channel, typically its width, and α is the surface tension of the fluid. For Bond numbers lower than 0.1, capillary forces serve as the primary driving forces, and gravity is of lesser influence. At Bond numbers above 10, gravity becomes the primary driving force. For Bond numbers between 0.1 and 10, both capillary and gravitational forces have a definitive effect that can compete, amplify, or alter one another. Finally, capillary and gravitational forces can be used in conjunction in the design of channels, so as to enhance and otherwise direct the flow of a collected fluid.

A channel can be narrow (less than 1 mm) of high capillary force (a low Bond number) or wide of high gravity force where the Bond number is higher. Subsequently, to drive the device by capillary forces, fluid may be readily drawn into the narrow channel due to the high capillary force that dominates gravity, which is ultimately based on channel geometry and measurements. The ability to utilize capillary and gravitational forces together to create efficient channels can result in devices that are simpler, less expensive, and easier to manufacture and more robust in their operation because they have higher working tolerances, therefore not requiring as much precision in the channels, which results in unit cost reduction. In preferred embodiments of the test strip/cartridge of the invention, fluid flow is driven by capillary force solely and channels can be designed with dimensions less than 1 mm permitting free positioning of the device during testing without the need for gravity driven flow, such as that needed to move fluid in a main channel of devices such as the HEMOLINK™ system.

The term "microfluidic filter" describes a filter comprising a porous or perforated surface used to process, purify, or otherwise manipulate a fluid constrained to a small (e.g., less than 5 mm) diameter. The term "pore" as used herein is defined to mean any opening through which matter, commensurate in size with or smaller than the opening, can pass. Dead-end filtration refers to filtration in which a fluid flow passes through a filtering surface that retains solid particles or cells in the fluid flow. An example would be passage of a flow of blood cells and plasma perpendicularly through a filter that retains blood cells but permits plasma to flow through the filter. There is no restriction of the blood-filtering material used in the invention. A single-type of dead-end filter may be used that progressively entangles large blood cells, then smaller blood cells, and then smaller blood components. Alternatively, a series of filters having different pore sizes may be used. The filters may entangle blood cells within them or trap blood cells at their surfaces. In some embodiments a glass fiber filter, a microporous membrane or combinations of both are used. Since the objective of the test strip/cartridge is to measure an enzymatic activity within red blood cells, the filter used to isolate red blood traps the blood cells at the surface of the filter for further analysis, evaluation and/or modification.

A glass fiber filter can have a density of about 0.02 to 0.5 g/cm$^3$, preferably about 0.03 to 0.2 g/cm$^3$, more preferably about 0.05 to 0.13 g/cm$^3$, and a retainable particle size of about 0.6 to 9 μm, preferably 1 to 5 μm. The surface of glass fiber filter may be treated with hydrophilic polymer to facilitate faster and smoother action. A lectin, anticoagulant, or other reactive reagent or modifier may be incorporated into the glass fiber or the glass fiber may be treated therewith. Two or more sheets of a glass fiber filter may be stacked.

Microporous membranes with hydrophilic surfaces may also be employed for separating blood cells from whole blood. A suitable pore size of the microporous membrane is smaller than the retainable particle size of a glass fiber filter but is preferably 0.2 μm or more, preferably about 0.3 to 5 μm, more preferably about 0.5 to 3 μm. A higher void content (e.g., the void content that passes through the membrane) of the microporous membrane is preferable, and a suitable void content is about 40 to 95%, preferably about 50 to 90%, more preferably about 70 to 85%. The microporous membranes include but are not limited to a polysulfone membrane, a fluorine-containing polymer membrane, a cellulose acetate membrane, and a nitrocellulose membrane.

Human red blood cells are disks of diameter 6-8 microns and thickness 2 microns and have an occurrence of approximately 5 million cells per μL of blood. Human leukocytes, comprising mostly neutrophils (approximately 60%, 10-12 micron diameter) and lymphocytes (about 30%, 7-8 microns diameter) have a total occurrence of about 4,000-11,000 cells per μL of blood. Human platelets (thrombocytes) are 2-3 micron diameter and have an occurrence of 150,000-400,000 cells per μL of blood. A red blood cell can pass through openings smaller than 6 microns by deformation and may be passed or excluded by selecting a size necessary to affect their physical separation from other blood components. For example, a set of openings of size 5 microns may block passage of most leukocytes, but may allow deformable red blood cells and platelets to pass. Analogously, a filter having a pore size of 2-3 micron can allow platelets to pass but block passage of red blood cells. Smaller pore size filters can be used to block passage of platelets and let plasma pass.

In one embodiment, the invention separates whole blood components and employs dead-end microfilters to sequentially remove blood cells having different sizes. For example, microfilters with different pore sizes are used to remove red blood cells having a disk diameters ranging from approximately 6.2-8.2 μm and a thickness at the thickest point of 2-2.5 μm; white blood cells including neutrophils and eosinophils ranging from about 10-12 μm; basophil and large lymphocytes ranging from about 12-15 μm; small lymphocytes ranging from about 7-8 μm; monocytes ranging from about 15-30 μm and platelets ranging from about 2-3 μm in greatest diameter. Microfilters may be selected to retain one or more of these kinds of cells and permit smaller cells and plasma to pass through. Preferably, larger cells are removed first. As plasma contains coagulants, an anticoagulant such as heparin, may be contained in a microfilter or in other portions of the microfluidic strip/cartridge to inhibit coagulation of blood cells while they are being sequentially removed from whole blood. In some embodiments the smallest or ultimate filter will have pore sizes of about 0.02 μm.

In some embodiments, the filtration system can process whole blood and produce red blood cells from small quantities of blood, such as 50, 25, 20, 15, 20, 10, 5, 4, or 3 μLs of whole blood. In preferred embodiments it will produce 1-5 μl of red blood cells. It is understood that the cell and pore size ranges above include all intermediate subranges and values, such as about 1, 2, 3, 4, 5, 6, 7, 8, 9, 10, 12, 15, 20, 25, and 30 μm in maximum or average diameter.

The pore sizes of sequential microfilters may be selected to improve the amount of red blood cells produced and to minimize clogging of the filters. Filtration may be powered by capillary forces and/or by micropumps arranged before or after filters. However, in some embodiments, the device will provide positive or negative pressure to the test strip/cartridge to allow blood and red blood cells to flow through test strip/cartridge.

The term "cross-flow filtration" refers to filtration in which a fluid flow direction is parallel to a filtering surface. An example would be flow of blood through a tubular conduit where the filtering surface forms the walls of the tube and is permeable to plasma but not blood cells. In this example, plasma would be removed in a direction away from the axis of the tube, while blood cells could continue movement through the tubular conduit. In some embodiments, the device of the invention will incorporate a cross-flow filter or separate blood cells from plasma by dielectrophoresis as described, for example, by Chen, et al., Lab. Chip, 2014, 14 (2014), Chen, et al., Microelectronic Engineering 128: 36-41 (2014), by Szydzik, Crispin, et al., Biomicrofluidics 9.6: 064120 (2015), or by Shim, et al., 14th International Conference on Miniaturized Systems for Chemistry and Life Sciences 3-7 Oct. 2010, pp. 145-147, which are incorporated by reference. The term "dielectric separation" refers to a method of separating different types of substances or cells based on a difference in charge that may be either inherent and/or induced. A dielectric separation can include, but is not limited to, separation of blood cells or other solid components of blood from plasma.

Dielectrophoretic methods for cell and particle separation are based on the polarization of suspended particles or cells. A microfluidic network using this method can be a capillary-driven, portable, and low voltage contactless dielectrophoresis (cDEP) plasma separation chip that can have asymmetric capacitive-coupled electrodes to induce inhomogeneous electrostatic forces in the microchannel and increase dipole-dipole interactions between the red blood cells. A cDEP plasma separation chip can separate plasma from undiluted human whole blood samples without any external driven force. The intensity of capillary forces affects plasma separation time and the velocity of the sample. In some embodiments blood cells may be separated from whole blood by dielectrophoretic methods as well as filtration, for example, red blood cells may be removed using dielectrophoresis and other blood components by filtration.

The blood sample collection zone has one or more capillary openings to receive the sample and allows the blood to flow toward the red blood cell isolation zone. In some embodiment, it contains an anticoagulant such as, but not limited to heparin to prevent the blood from clotting and clogging the passage way of the test strip/cartridge.

The red blood cell isolation zone comprises one or more filters that retain red blood cells and function to remove one or more components of the blood. In some embodiments, one filter with large pore removes white blood cells larger than 7 micron and a second filter with fine pores of less the 5 micron removes plasma and platelets. Since TPMT is found only in red blood cells, the presence of other cells with the red blood cells is not critical for the measurements of TPMT activity. The filtration system can be any filtration system so long as it retains red blood cells in the flow through of the sample. In some embodiments, a cross flow filtration system is preferred, whereas a dead-end filtration system is preferred in other embodiments. Yet in some other embodiments, a combination of cross flow filtration and dead-end filtration is preferred.

The lysis zone of the test strip or cartridge comprises at least one lysing agent. Any lysing agent may be used at any concentration as long as it does not denature and/or inactivate the enzyme. The amount of the lysing agent can be adjusted to a concentration of lysing agent that lyses the red blood cells without denaturing and inactivating the enzyme. In some embodiments, the lysing agent is selected from the group consisting of detergents, ammonium salt, and combinations thereof.

Many detergent lysing agents are known in the art including, but not limited to, polyethylene glycol p-(1,1,3,3-tetramethylbutyl)-phenyl ether $[C_{14}H_{22}O(C_2H_4O)_n]$ commercially available in two forms known as Triton X-100 and Triton X-114, nonyl phenoxypolyethaoxylethanol better known as NP-40, $(C_2H_4O)_nC_{12}H_{26}O$ known as Brij-35, $HO(CH_2CH_2O)_{20}C_{16}H_{33}$ known as Brij-58, polyoxyethylene (20) sorbitan monolaurate known as Tween 20, polyoxyethylene (20) sorbitan monooleate known as Tween 80, octyl glucoside, octyl thioglucoside, sodium dodecyl sulfate (SDS), 3-[(3-cholamidopropyl)dimethylammonio]-1-propanesulfonate (CHAPS), sodium deoxycholate, saponin, and 3-[(3-cholamidopropyl)dimethylammonio]-2-hydroxy-1-propanesulfonate (CHAPSO).

Compositions comprising ammonium salts and alkali metal ions alone or in combination with negatively charged detergent such as, but not limited to lithium lauryl sulfate (LLS), are known to selectively lyse red blood cell while keeping white blood cells intact. See for example U.S. Pat. Nos. 4,185,964 and 10,093,989, both incorporated herein by reference in their entirety. These patents disclose lysing compositions comprising ammonium salts, lithium lauryl sulfate (LLS), and an anticoagulant which selectively lyses red blood cell and leaves other blood cells intact. The ammonium salt has the chemical formula $R_1N^+(R_2)_3X^-$ where $R_1$ and $R_2$ are independently H or alkyl group of 4 to 18 carbon atoms, and X is any counter ion such as, but not limited to chloride, bromide, fluoride, iodide, acetate, and citrate. Other reagents may be present such as, but not limited to reducing agents and buffers. Many reducing agents are known in the art including disulfide bond reducing agents such as but not limited to 2-mercaptoethanol, 2-mercaptoethylamine hydrochloride, cysteine, dithiothreotol, glutathione, and tris(2-carboxyethyl)phosphine hydrochloride. The buffer may be any buffer having good buffering characteristics without being an inhibitor of TPMT in the range of pH 6 to 8 such as, but not limited to phosphate buffer, Tris buffer, MOPS, imidazole buffer, and glycine buffer.

In a preferred embodiment the test strip/cartridge, both red and white cells are separated from the plasma by the filtration system and treated with a lysing agent to preferentially lyse the red blood cells. In such an embodiment, a dead end filtration system is deployed between the lysing zone and the reagent mixing zone which allows only or mostly red blood cell lysate to flow to the reagent mixing zone.

Figure 5:
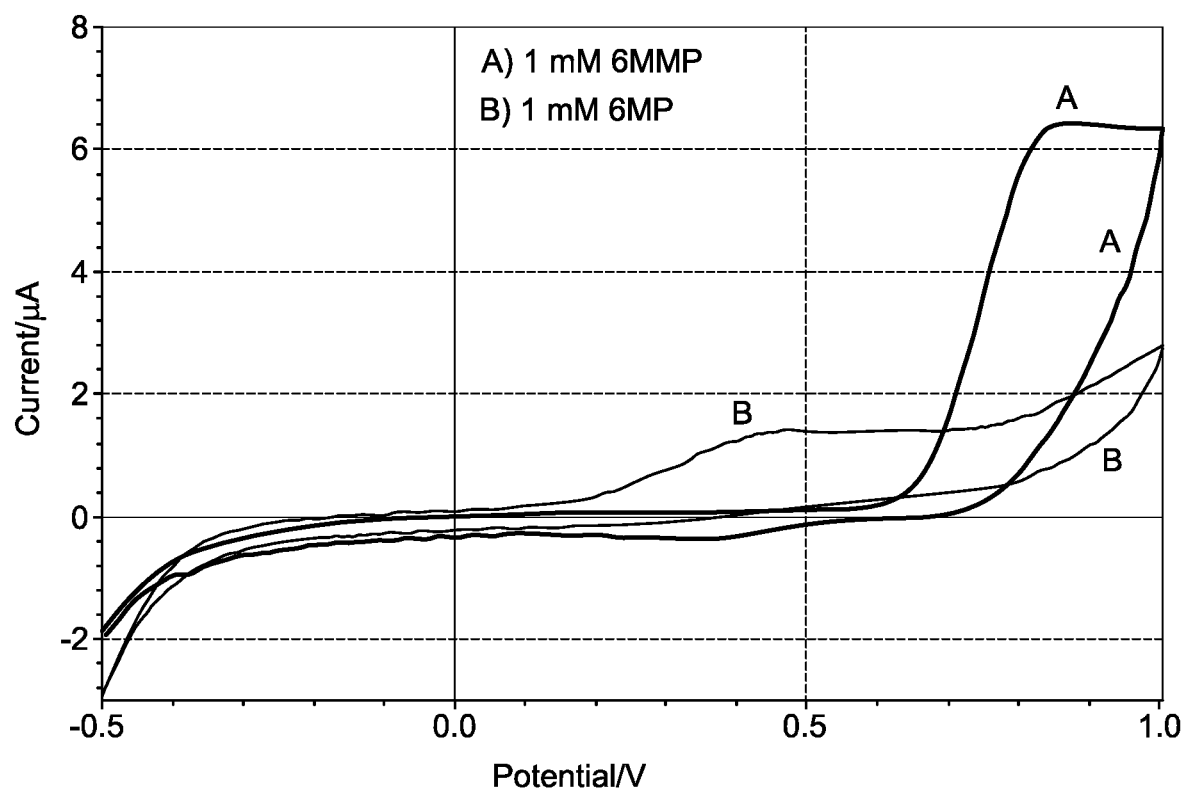
FIG. 5 shows current voltammetry: Curve (A) is 1 mM 6 MMP and Curve (B) is 1 mM 6 MP.

The reagent mixing zone contains a mercaptopurine compound and S-adenosylmethionine (SAM) and optionally a buffer. The substrate can be any mercaptopurine compound provided that it is a substrate for TPMT. Examples of known substrates for TPMT are 6-mercaptopurine (6-MP) and 6-thioguanine. (6-TG). Any concentration of the substrate may be used as long as the reaction mixture produces sufficient signal in the sensing zone. In a preferred embodiment, the concentrations of the mercaptopurine compound and SAM are preferably much larger than the $K_m$ value for the enzymatic reaction, i.e., the substrates are saturating the enzyme active site. At a saturating concentration of substrates, the reaction displays zero order kinetics and the reaction rate is directly proportional to the amount of enzyme in the sample The sensing zone contains a detection system to detect the appearance one or more products of the reaction or the disappearance of one or more of reactants. The detection system may be any detection system such as but not limited to optical detection system or an electrochemical detection system. A large UV/vis or fluorescent spectral change preferably accompanies the methylation reaction. One of the products of the methylation reaction is a proton (see FIG. 2), and thus, a change of pH can be measured electrochemically and may be correlated to TPMT activity provided that the sample does not contain any buffer. Sulfur-containing compounds are amenable to electrochemical oxidation reactions by an electrode system. The various substrate and products produced by TPMT-catalyzed reaction can be distinguished and the concentration of each compound may be quantified by oxidation peaks potential for example in a square wave voltammogram. Standard 1 mM solutions of 2-amino-6-methylmercaptopurine (6 MMP) and 6-mercaptopurine monohydrate (6 MP), both purchased from Sigma Aldrich, dissolved in PBS containing 0.01M Phosphate, 0.0027M potassium chloride, 0.137M Sodium chloride, pH 7.4. The cyclic voltammograms were record between −0.5 V and 1.0 V v. reference at a scan rate of 50 mV/s. FIG. 5 shows the cyclic voltammogram for 1 mM solutions of 6-MP (curve A) and 6-MMP (curve B) in PBS, pH 7.4. In an assay 6-MP is methylated by the action of TPMT to produce 6-MMP. The enzymatic activity can be estimated from the observed change of the signal of the cyclic voltammogram.

A second aspect of the invention is directed to a device for measuring the activity of thiopurine S-methyltransferase (TPMT) in a biological fluid comprising:

a meter comprising a display, a signal processor, and a memory card, and the test strip or cartridge disclosed herein, wherein the device has temperature controlled compartment for the sensing zone and the sensing zone of the device is operatively connected to the processor and the display.

In some embodiments, the meter is able to generate monochromatic light at a specific wave length in the UV/vis range which is absorbed by the substrate or the product. The light is designed to go through the sensing zone from one side and exit from the other side where a detector measures a change in light intensity. The change in light intensity or change in fluorescence intensity directly correlates with change in concentration of the substrate or the product of the reaction being observed. For example, Beer's Law provide the relationship between optical density and the concentration of a compound according to the equation: $A=\varepsilon LC$, where A is the measured change in optical density (absorption), $\varepsilon$ is molar absorption coefficient, L is the light path length in the sample, and C the molar concentration. Alternatively, a detector is located perpendicular to the beam of light to sense a sample fluorescence.

The meter is portable and contains an opening where the strip/cartridge can be inserted and connected to the meter. It is configured to detect one or more signals produced by the sensors in or near the sensing zone. It includes a processor configured to process an optical or electrochemical signal. In some embodiments, the processor is capable of processing a change in optical signal over a preset period of time to calculate the rate of a reaction. In a more preferred embodiment, the processes or is configured to process an electrochemical signal due to change in pH or change in oxidation potential over a period of time. The results of the processed signal is displayed on an output such as screen or print out.

In a more preferred embodiment, the meter is connected to electrodes imbedded in the sensing zone to measure the increase in hydrogen ion concentration or the oxidation potential of a substrate and/or a product.

The meter of the invention contains a temperature control system able to maintain a constant temperature of the sensing zone in the range of 20 to 40° C., preferably in the range of 25 to 40° C., more preferably in the range of 30 to 40° C., and most preferably at 37° C.

Also, the meter is programed to process an optical signal or an electrochemical signal to a change in the molar concentration of a substrate and/or a product per unit time display the result on the meter.

A third aspect of the invention is directed to a method for detecting and measuring TPMT activity in blood comprising contacting a blood sample from a subject with a test strip or cartridge connected to the meter described herein and read the results on the display of the meter. As indicated previously, the blood sample may be collected by any means known in the art. It may be introduced to the test strip/cartridge by any mean. In some embodiments, the sample may be injected directly into the blood collection zone using a syringe or pump. In a more preferred embodiments, the sample is obtained finger stick and directly contacted with the opening of the blood sample collection zone to allow the sample to flow through the sample collection zone by the capillary action.

The subject may be any mammal or other animal in need of treatment by a thiopurine compound. The mammal may be a farm animal or a pet such as but not limited to a cat, a dog, cow, sheep, goat, and horse. In a more preferred embodiment, the mammal is human.

The invention claimed is:

1. A microfluidic test cartridge for measuring the activity of thiopurine S-methyltransferase (TPMT) in a blood sample comprising:
   in the following order, connected by a microfluidic path:
   a blood sample collection zone having a volume of from 100 μL mL to 900 μL,
   a red blood cell isolation zone having a volume of from 20 μL to 400 μL,
   a lysis zone having a volume of from 20 μL to 50 μL,
   a reagent mixing zone having a volume of from 10 μL to 30 μL, and
   a sensing zone having a volume of from 5 μL to 15 μL,
   wherein the microfluidic test cartridge is configured so that a blood sample passes sequentially from one zone to another by capillary action, and
   wherein the red blood cell isolation zone comprises a filtration system comprising two stacked glass fiber sheets each incorporated with lectin,
   wherein the lysis zone comprises an ammonium salt as a lysing agent, wherein the ammonium salt is of formula $R_1N^+(R_2)_3X^-$ where $R_1$ and $R_2$ are independently H or an alkyl group of 4 to 18 carbon atoms, and X is selected from the group consisting of chloride, acetate, and phosphate,
   wherein the reagent mixing zone comprises at least one mercaptopurine compound selected from the group consisting of 6-mercaptopurine and 6-thioguanine, and
   wherein the sensing zone comprises one or more embedded electrodes.

2. The test cartridge of claim 1, wherein flow of blood from the collection zone through filtration system to the sensing zone is driven by capillary forces.

3. The cartridge of claim 1, comprising a series of micropumps that can drive blood when present in the cartridge through the filtration system, the lysis zone, the reagent mixing zone and to the sensing zone.

4. The test cartridge of claim 1, further comprising a filter between the lysis zone and the reagent mixing zone to separate red blood cell lysate from intact white blood cells.

* * * * *